United States Patent [19]

Augustine et al.

[11] Patent Number: 4,572,188

[45] Date of Patent: Feb. 25, 1986

[54] AIRFLOW COVER FOR CONTROLLING BODY TEMPERATURE

[76] Inventors: Scott D. Augustine, 4761 Olive St., San Diego, Calif. 92105; Douglas J. Augustine, 414 Washington St., Sandstone, Minn. 55072

[21] Appl. No.: 586,554

[22] Filed: Mar. 5, 1984

[51] Int. Cl.<sup>4</sup> .............................................. A71F 7/00
[52] U.S. Cl. .................................... 128/380; 4/536; 4/537; 34/99; 62/261; 126/204; 128/400; 165/46
[58] Field of Search .............. 128/367, 368, 379, 380, 128/400, 402; 4/535, 536, 537; 34/99, 233, 243 R; 219/212; 165/46; 62/259.3, 261; 2/171.3; 126/204

[56] References Cited

U.S. PATENT DOCUMENTS

| | | | |
|---|---|---|---|
| 2,093,834 | 9/1937 | Gaugler | 4/536 |
| 2,110,022 | 3/1938 | Kliesrath | 5/334 |
| 2,601,189 | 6/1952 | Wales | 219/212 X |
| 2,706,988 | 4/1955 | Weber | 128/402 |
| 3,418,726 | 12/1968 | Sparks | 34/99 |
| 3,757,366 | 9/1973 | Sacher | 5/347 |
| 3,881,477 | 5/1975 | Von Otto | 128/132 |
| 3,908,655 | 9/1975 | Lund | 128/256 |
| 4,398,535 | 8/1983 | Guibert | 128/399 |

OTHER PUBLICATIONS

Product Bulletin Nos. 1178A, 1181 and 677 for Cincinnati Sub-Zero.
Product Bulletin for Product Part MTA 4700 to Gaymar Industries, Inc.

*Primary Examiner*—Anton O. Oechsle
*Attorney, Agent, or Firm*—Brown, Martin & Haller

[57] ABSTRACT

An airflow cover for controlling the body temperature of a patient covers a portion of the patient's body and provides a generalized thermal bathing of the covered portion through the delivery of a temperature controlled gas mixture to the covered portion. The cover is formed from a series of inflatable tubes which are joined together in a parallel array having an upper surface facing away from the patient's body and an oppositely directed lower surface which faces the covered portion of the patient's body. An entry port is provided through the upper surface and into one tube, transverse ports open between the tubes, and exit ports are formed in the lower surface. A thermally controlled gas mixture is introduced through the entry port, circulates in the tubes by means of the transverse ports and inflates the tubes, and exits through the exit ports in the direction of the covered body portion to provide the desired thermal bathing.

10 Claims, 4 Drawing Figures

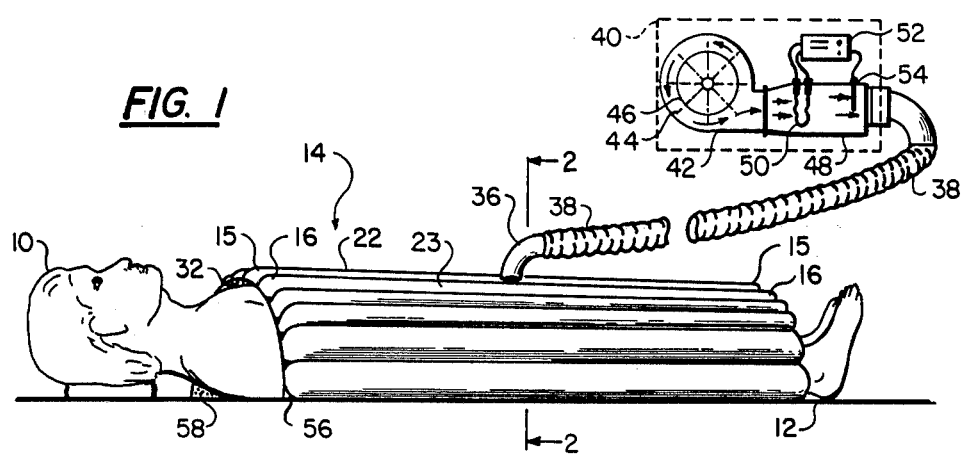
FIG. 1
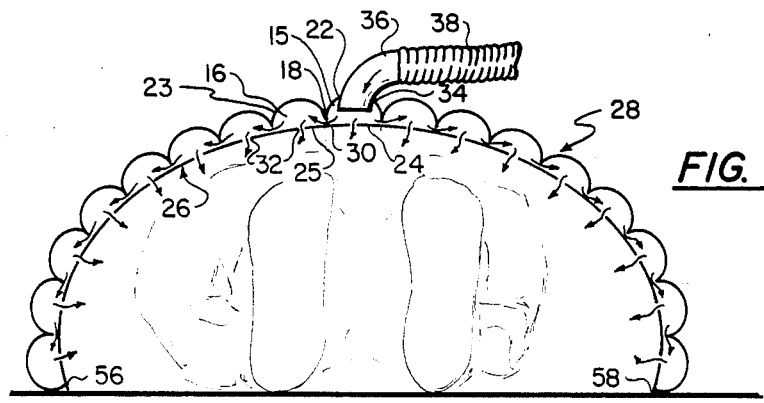
FIG. 2
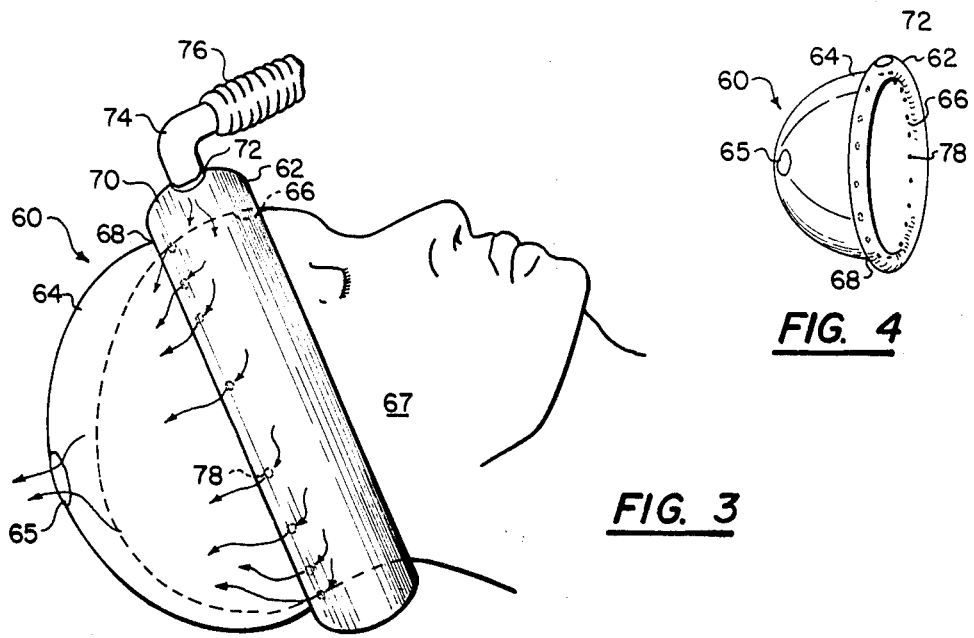
FIG. 3
FIG. 4

AIRFLOW COVER FOR CONTROLLING BODY TEMPERATURE

BACKGROUND OF THE INVENTION

The cover of the invention relates generally to a cover used in a medical treatment environment to control the bodily temperature of a patient, and more specifically to such a cover which controls the temperature of a covered patient's body by bathing it with a temperature controlled gas mixture.

It is often the case that the bodily temperature of a patient who is about to undergo or who has undergone certain forms of medical treatment such as surgery must be regulated by lowering or elevating it to a predetermined average level. In existing apparatus, the generalized control of such a patient's temperature is provided by means of a pliable blanket through which a temperature controlled fluid is circulated. When the patient is covered with such a blanket, the temperature of the fluid is conducted to the patient to move the patient's temperature toward the desired level. However, most of the temperature exchange between the blanket and the patient takes place only at the points where the blanket contacts the patient's skin. This can result in localized thermal activity of a high rate where the blanket and the patient's skin are in contact, which results in the localized temperature of the contacted portion of the patient's body being either substantially above or below the desired average temperature. When the patient's body temperature is being elevated and the circulating fluid is heated, this can result in burning at the contacted areas. In addition, the heat transfer between the blanket and the portions of the patient's body which the blanket does not contact is radiative and therefore inefficient.

In other covers, the circulating heat transfer mechanism is temperature controlled air. In one such cover disclosed in U.S. Pat. No. 2,110,022, the air is circulated inside of a flexible bag which has a top insulating layer and a bottom heat conducting layer which contacts the patient. However, the structure of this blanket makes it unnecessarily heavy and rigid. The weight of the blanket can press its inner surface against the covered patient and block a number of the exit ports, thereby reducing the total body area over which the air circulated.

It is therefore desirable to provide a supple, lightweight cover for efficiently and effectively controlling the bodily temperature of a covered patient.

SUMMARY OF THE INVENTION

The cover of the present invention overcomes the limitations of existing covers which control the bodily temperature of the patient by providing a lightweight flexible, inflatable casing having an upper and a lower surface. The casing has an entry port penetrating its upper surface for permitting a thermally-controlled inflating medium to flow into and inflate the casing, and a plurality of exit ports formed in the lower surface for, when the casing is inflated, permitting the thermally-controlled medium to flow out of the casing's lower surface. The cover is placed over a patient and inflated by introduction of the medium through the entry port into a self-supporting structure which encloses the patient. The temperature-controlled inflating medium circulates through the inflated casing and exists through the exit ports on the lower surface which faces the patient to provide the desired generalized thermal bathing of the patient's body.

Preferably, the casing is made from a plurality of enlongated inflatable tubes, each of which is formed from a lightweight flexible material such as plastic. The tubes are joined together longitudinally to form a substantially parallel array, the opposing major surfaces of which form the upper and lower surfaces of the cover. An entry port is provided in the upper surface; transverse ports are provided between adjoining tubes; and a plurality of exit ports are provided in the lower surface of the array. The tubular structure of the cover and the material from which the tubes are formed enable the casing to inflate and to form a self-supporting structure when the cover is laid atop the patient. The tubular construction causes the cover to naturally wrap around the patient and provide a semi-enclosed, generally tubular structure which covers the patient. The inflating medium is preferably a gas mixture which is provided under pressure from a unit which exchanges energy with the mixture. The light weight of the casing permits it to be partially supported by the air escaping through the exit ports which prevents the cover from blocking the ports by contacting the covered body portion.

The unit is connected to the input port by means of a delivery hose and has a blower assembly for forcing the mixture into the cover. In the preferred embodiment, the gas mixture constitutes ambient air which is heated to a desired temperature level and blown through the delivery hose to the cover and delivered therefrom through the exit ports to thermally bathe the patient.

It is therefore the principal object of the present invention to provide an airflow cover which controls the body temperature of a patient by delivering a diffused flow of a thermally-controlled gas mixture which results in a generalized thermal bathing of the patient.

It is a further object of the present invention to provide such a cover which is inflated by the temperature-controlled mixture into a self-supporting structure which substantially encloses the patient and thereby increases the efficiency of the generalized thermal bathing.

Other objects and advantages of the present invention will become apparent when the description of the preferred embodiment is read in conjunction with the following drawing figures:

BRIEF DESCRIPTION OF THE DRAWINGS

FIG. 1 is a side view of the airflow cover of the invention in a representative operational environment.

FIG. 2 is a partial sectional view of the cover of the invention with the cross section of the cover taken along lines 2—2 of FIG. 1.

FIG. 3 is an illustration of a representative application environment for a second embodiment of the airflow cover of the invention where the cover is used to thermally bathe a portion of a patient's body.

FIG. 4 is a perspective view of the embodiment illustrated in FIG. 3.

DETAILED DESCRIPTION OF THE PREFERRED EMBODIMENTS

With reference to FIG. 1, the reader will understand the operational application of the preferred embodiment of the air-flow cover of the invention. In FIG. 1 a patient 10 is shown reclining on a surface which may comprise the upper surface of a gurney or a bed. Surrounding the patient is the cover of the invention, illustrated generally by 14, which is shown placed over the patient and inflated into a substantially semi-tubular structure which encloses the major portion of the patient's midbody. In the illustsrated operational application, the cover 14 is delivering a diffused stream of heated air by means disclosed in greater detail hereinbelow to the enclosed portion of the patient's body. Such an application would be useful, for example, where the patient's temperature has dropped below a medically safe average to a point where a peril of hypothermia is presented. In such a circumstance, it is desired to quickly and efficiently raise the patient's temperature in order to restore the temperature to as near normal as is possible.

The means by which the cover 14 accomplishes the desired purpose can be understood with reference to FIGS. 1 and 2. The cover 14 is made up of a plurality of parallel elongate plastic tubes, two of which are indicated by 15 and 16, interconnected to form an inflatable casing. It is to be understood that the description of the tube 16 precisely describes the remaining tubes which form the cover. As illustrated, the tubes 15 and 16 are joined together by a intermittent longitudinal seam 18. Each tube is formed from a flexible inflatable material, such as plastic. The use of plastic to form the tubes 15 and 16 permits the seal 18 to consist of either a heat seal or a cured epoxy seal which is sufficient to join the tubes as indicated. The tubes 15 and 16 have half-rounded cross-sectional shapes with rounded upper portions 22 and 23, respectively, and flattened lower portions 24 and 25, respectively. The lower flattened portions of all of the joined tubes together form a lower surface 26 and the rounded upper portions, a generally longitudianlly quilted upper surface 28.

One or more transverse openings or ports 30 are provided through the seam 18 and through all of the seams to permit an inflating medium such as air to circulate between the tubes. A plurality of exit ports 32 are provided in the lower flattened portions of all of the tubes which permit the circulating medium to flow out of the tubes and through the lower cover surface 26. Although the ports 30 and 32 are shown aligned in FIG. 2, it should be evident that they may be alternately staggered into the plane of the cross section so that the illustration would then show alternate tubes with ports, the ports of the non-ported tubes being out of the plane of the section. A single input port 34 in the keystone tube 15 accepts the end nozzle 36 of a delivery hose 38, which is connected to a heater/blower assembly 40. The assembly includes a blower housing 42, a fan 44, and a motor 46 which is coupled to rotate the fan 44. The housing 42 is connected to and communicates with a heating manifold 48 in which is disposed a heating element 50 connected to a standard temperature controller 52. A thermistor probe 54 is also disposed in the manifold 48 between the heating element 50 and the end of the delivery hose 38.

In operation, the heater/blower assembly 40 causes air heated to a predetermined temperature to be blown through the delivery hose 38 and the nozzle 36 into the keystone tube 15 of the cover 14. The temperature-controlled air circulates from the keystone tube 15 through the transverse ports 30 into all of the other tubes which form the cover 14. The heater/blower 40 is operated to provide an input flow of heated air which has sufficient pressure to fully inflate all of the tubes of the cover 14 without causing any of them to burst. As the heated air flows into the tubes and inflates them, the inflation pressure causes the heated air to be forced out of the exit ports 32. The air which is blown from the exit ports 32 provides the generalized thermal bathing of the patient 10. The arrows in FIG. 2 indicate the direction of circulation of the air from the delivery hose 38 through the cover 14 to the patient 10. When the cover 14 is placed over the patient 10 and inflated, the pressure of one tube against another is collected at the edges 56 and 58 of the cover which causes the edges to curl down around the patient toward the surface 12. However, the inflation of the tubes provides the cover 14 with a self-supporting structure having a generally rounded or elliptical cross-sectional shape which contacts the patient 10 only at the tubes which are immediately adjacent the keystone tube 15. The lightweight material from which the tubes are formed permits the air pressure which is exerted through the exit ports 32 of those tubes which are in contact with the patient to raise those tubes slightly so that circulation is provided through those exit ports. This is in contrast with the heavy structures of the existing airflow covers whose weight and structure block the ports which contact the patient. The cross-sectional structure illustrated in FIG. 2 enables the cover 14 to diffuse the temperature-controlled air which is delivered through the hose 38 into a generalized airflow which bathes as much of the patient's body as is covered by the cover 14. This convective operation increases the effectiveness and efficiency of the thermal exchange between the patient and temperature-controlled air without causing the localized thermal exchange of the existing circulating water blankets.

An alternate embodiment of the airflow cover of the invention is illustrated in FIGS. 3 and 4 wherein a scalp air-flow cover 60 includes an inflatable annular tube 62 to which is joined a generally rounded cap or enclosure 64 having an exit port 65. The annular tube has an inner surface 66 forming an opening which is placed over a portion of the head of a patient 67. Both the tube 62 and the cap enclosure 64 are constructed from a lightweight, flexible material, such as thermally-formed sheet plastic. The two pieces are joined by a continuous air-tight seam 68. The annular tube 62 has an outer surface 70 through which a port 72 is provided which accepts the nozzle 74 of a delivery hose 76. The delivery hose 76 is connected to a heater/blower assembly (not shown) which is identical in all respects to the heater/blower assembly 40 of FIG. 1. On the inner surface 66 of the annular tubes 62 and adjacent the seam 68, a plurality of exit ports 78 are provided. The exit ports are formed in the tube to be on the interior of the heating cap 60 when it is placed on the head of the patient 61. In operation, when pressurized or flowing air is introduced through the delivery hose 76, the annular tube 62 is inflated, with the inflating air being forced under pressure out of the exit ports 78. When the tube 62 is inflated it forms a contact barrier between itself and the head of the patient 67 so that air which flows out of the exit port 78 is forced into the end portion 64, circulates therein and exits through the end portion exit port 65. Thus, the annular tube 62 diffuses the flow of air delivered by the hose 76, with the tube and the end portion 64 providing a generalized thermal bathing of the scalp and head of the patient 67. It should be evident that when the tube 62 inflates, it slightly raises the head of the patient 67, thereby providing an air passage between the lower portion of the patient's head and the end portion 64. It should be further evident that this maximizes the area of the patient's scalp which is thermally bathed.

Although the embodiments of the invention are described as operating in conjuction with heated air, it should be evident to those skilled in the art that a source of pressurized cooled air will provide a generalized cooling bath using either of the cover embodiments described hereinabove to control the body temperature of the patient under conditions of hyperthermia. Moreover, it should be evident that, while the inflating and bathing mixture was described as heated air, any medium which is sufficiently vaporized can be used to inflate either embodiment of the cover and to provide the generalized thermal bathing. Moreover, it is possible to suspend an aerosal in the inflating and circulating medium, which can include a disinfectant for treatment of burned areas of the patient's body.

Obviously, many modifications and variations of the described embodiments are possible in light of the above teachings, and it is therefore understood that the invention may be practiced otherwise than as specifically described.

We claim:

1. A cover for delivering a diffuse medium flow to a human body, comprising:
   an inflatable cover housing including a plurality of inflatable hollow tubes, each tube having a rounded upper portion and a flattened lower portion, joined in a substantially parallel array to form a substantially smooth lower cover surface including said lower tube portions for facing a body to be covered and a quilted upper cover surface including said upper tube portions for facing away from said body;
   an entry port in said upper surface for admitting an inflating medium into said housing;
   transverse openings connecting the interior of each tube with the interior of at least one other adjacent tube in said array for conducting an inflating medium into all of said tubes to inflate said housing; and
   exit ports formed in the flattened portion of each of said tubes for, when said housing is inflated, permitting said medium to flow out of said housing through said smooth lower surface.

2. The covering of claim 1 further including a source of a thermally controlled, inflating meduim connected to said entry port means.

3. The covering of claim 2 wherein said medium comprises a gas mixture.

4. The covering of claim 3 wherein said gas mixture comprises air.

5. The covering of claim 1 wherein, when said housing is inflated and placed over a body, said housing assumes a tubular, self-supporting structure for substantially enclosing said body.

6. The covering of claim 1 wherein each said exit opening is substantially smaller than said entry opening.

7. The covering of claim 6 further including a source of a pressurized, thermally controlled gas mixture connected to said entry port means, wherein said thermally controlled gas mixture enters said array through said entry port, inflates said housing, and flows out from said inflated housing through said exit ports.

8. A cap for controlling the temperature of the head of a reclining person, comprising:
   an inflatable annular tube forming a central opening for encirclingly fitting to the head of a person reclining on a support surface and for being inflated to lift said head from said surface;
   a sheet of material attached to one side of said annular tube over said central opening to form a recess for receiving substantially the top of a head when said head extends into said recess through said central opening;
   an outer surface on said tube;
   an entry port on said tube outer surface for admitting a temperature-controlled, inflating medium into said tube;
   an inner surface in said tube's central opening;
   exit ports in said inner surface for, when said tube is inflated with an inflating medium, conducting said inflating medium from said tube into said recess; and
   an exit port, substantially smaller than said central opening, in said material sheet for venting an inflating medium from said recess to an external environment.

9. The cap of claim 8 further including a source of thermally controlled, inflating medium connected to said entry port.

10. The cap of claim 9 wherein said medium comprises a gas mixture.

* * * * *